United States Patent [19]

Eakin et al.

[11] Patent Number: 4,533,672

[45] Date of Patent: Aug. 6, 1985

[54] AMINO, CYANO PHENYLTHIO OR PHENOXYL INDOLE DERIVATIVES

[75] Inventors: Murdoch A. Eakin; Anthony J. Hayter; Barrington J. A. Furr, all of Macclesfield, England

[73] Assignee: Imperial Chemical Industries plc, London, England

[21] Appl. No.: 545,010

[22] Filed: Oct. 24, 1983

[30] Foreign Application Priority Data

Oct. 28, 1982 [GB] United Kingdom ............... 8230765

[51] Int. Cl.³ .......................................... C07D 209/42
[52] U.S. Cl. ........................................ 514/415; 548/483
[58] Field of Search ......................... 548/483; 424/274

[56] References Cited

FOREIGN PATENT DOCUMENTS

| 793358 | 6/1973 | Belgium . |
| 2131826 | 11/1972 | France . |
| 1045988 | 10/1966 | United Kingdom . |
| 179320 | 2/1965 | U.S.S.R. . |

OTHER PUBLICATIONS

Atassi & Tagnon, *European J. Cancer*, 1975, 11, 599–607.
Gilman et al., *J. Organic Chemistry*, 1972, 37, 3201–3206.
Gewald & Hentschel, *J. Prakt. Chem.*, 1976, 318, 663–670.
Aurich & Weiss, *Annalen Chem.*, 1976, 432–439.
Miyadera et al., *Chem. Pharm. Bull.*, 1981, 29, 2193–2198.
Shredor et al., "Synthesis . . . 2-Amino-3-Cyano-Tetrahydroindole," *Chem. Abst.* 84 (21): 150590r.

*Primary Examiner*—Donald G. Daus
*Assistant Examiner*—G. Hendricks
*Attorney, Agent, or Firm*—Cushman, Darby & Cushman

[57] ABSTRACT

This invention relates to indole derivatives which have anti-cancer activity. According to the invention there is provided an indole derivative of the formula I:

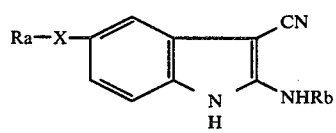

in which X is an oxygen or sulphur atom, Ra is a phenyl radical which is optionally substituted by one or two groups selected from halogen atoms and 1–6C alkyl, 1–6C alkoxy and trifluoromethyl radicals and Rb is a hydrogen atom or a 2–6C alkoxycarbonyl radical. Manufacturing processes and pharmaceutical compositions are also described.

6 Claims, No Drawings

AMINO, CYANO PHENYLTHIO OR PHENOXYL INDOLE DERIVATIVES

This invention relates to indole derivatives which have anti-cancer activity.

It is known from the *European Journal of Cancer*, 1975, 11, 599–607 that methyl[5-(thien-2-ylcarbonyl)-1H-benzimidazol-2-yl]carbamate (nocodazole, oncodazole) has anti-cancer activity. A related compound, methyl(5-phenylthio-1H-benzimidazol-2-yl)carbamate(fenbendazole), is a veterinary anthelmintic (Belgian Pat. No. 793358). It has now been discovered that a certain 2-amino-3-cyano-5-substituted indole derivative has anti-cancer activity.

According to the invention there is provided an indole derivative of the formula I:

[Formula I—given hereafter]

in which X is an oxygen or sulphur atom, Ra is a phenyl radical which is optionally substituted by one or two groups selected from halogen atoms and 1–6C alkyl, 1–6C alkoxy and trifluoromethyl radicals and Rb is a hydrogen atom or a 2–6C alkoxycarbonyl radical.

A particular value for the optional substituent on Ra is a fluorine, chlorine or bromine atom or a methyl, methoxy or trifluoromethyl radical.

Ra is preferably an unsubstituted phenyl radical.

A particular value for Rb is a hydrogen atom or a methoxycarbonyl or ethoxycarbonyl radical.

Rb is preferably a hydrogen atom.

The preferred compound of the invention is that of formula I in which X is a sulphur atom, Ra is an unsubstituted phenyl radical and Rb is a hydrogen atom, namely 2-amino-3-cyano-5-(phenylthio)indole.

The indole derivative of the invention may be manufactured by methods in which the actual chemical reactions involved are known in themselves. The following processes in which Ra, Rb and X have the meanings stated above, unless indicated otherwise, are therefore provided as a further feature of the invention. The process is characterised by:

(a) for those compounds in which Rb is a hydrogen atom, reduction of the nitro radical in a salt of a compound of the formula II:

[Formula II]

followed by ring-closure of the product, of the formula III:

[Formula III]

This ring closure may occur spontaneously. The salt may, for example, be a sodium or potassium salt. The reduction may be carried out by any standard method for reducing an aromatic nitro group which is compatible both with the stability of the starting material and the product. Thus the reduction may be carried out by catalytic hydrogenation at atmospheric pressure or up to 100 bar. The catalyst may, for example, be palladium on carbon or Raney nickel. Other reducing agents which may be used are Raney nickel and hydrazine, aqueous titanous chloride, and palladium on carbon and sodium borohydride. The preferred reducing agent is sodium dithionite. This agent may be used in aqueous solution preferably containing enough of a water-miscible organic solvent to ensure solution of the starting material. It is also preferable that a base such as ammonium hydroxide, sodium carbonate or sodium bicarbonate is present. A particularly preferred reducing agent is sodium dithionite and sodium bicarbonate in aqueous dimethyl formamide.

(b) reaction of a compound of the formula IV:

[Formula IV]

in which Rc is a chlorine or bromine atom with cuprous cyanide;

(c) for those compounds in which Rb is a hydrogen atom, reaction of a compound of the formula V:

[Formula V]

in which Rd is a chlorine or bromine atom or a 1–6C alkanesulphonate (e.g. methanesulphonate), benzenesulphonate or toluene-p-sulphonate radical with ammonia or a metal amide such as sodamide or potassamide;

(d) for those compounds in which Rb is an alkoxycarbonyl radical, reaction of a compound of the formula I in which Rb is a hydrogen atom with a compound of the formula PhOCOORe in which Re is a 1–5C alkyl radical;

(e) for those compounds in which Rb is an alkoxycarbonyl radical, replacement by hydrogen of the alkoxycarbonyl radical on the indole nitrogen in a compound of the formula VI:

[Formula VI]

in which Re is a 1–5C alkyl radical;

(f) for those compounds in which Rb is an alkoxycarbonyl radical, reaction of a compound of the formula VII:

[Formula VII]

in which Re is a 1–5C alkyl radical with phenoxide anion.

The compound of the formula II for use in process (a) may be prepared by reaction of 5-chloro-2-nitroaniline with the anion derived from the appropriate optionally-substituted phenol or thiophenol. The amino group is then replaced by a chlorine atom using a Sandmeyer reaction and the product is finally reacted with malononitrile. The last two reactions are illustrated in Example 1.

The compound of the formula IV for use in process (b) may be prepared by halogenation in the 3-position of a 2-ethoxycarbonylindole, transformation of the ethoxycarbonyl radical to an amino radical by standard methods and reaction of the amino radical with an alkyl phenyl carbonate.

The compound of the formula V for use in process (c) may be prepared by reaction of the corresponding oxindole with cyanogen bromide followed by halogenation of the product, or reaction with the appropriate sulphonyl chloride.

The compound of the formula VI for use in process (e) may be prepared by reaction of the compound of the formula I in which Rb is a hydrogen atom with at least two moles of an alkyl chloroformate.

The compound of the formula VII for use in process (f) may be prepared by reaction of the compound of the formula I in which Rb is a hydrogen atom with one mole of an alkyl chloroformate.

The compound of the formula II for use in process (a) is a particularly valuable intermediate, and this compound is provided as a further feature of the invention.

As noted above, the indole derivative of the formula I has anti-cancer activity, and in particular it is, like the vinca alkaloids, a spindle poison. The anti-cancer activity may be demonstrated in standard tests, for example by the ability of the compound of the formula I to retard or prevent the growth of implanted tumours in laboratory animals such as mice or rats, or to increase the survival time of mice which have been injected intraperitoneally with a suspension of cancer cells. Alternatively, the activity may be demonstrated by the ability of the compound of the formula I to prevent cell division in cell culture.

The anti-cancer activity of the preferred compound of the invention, 2-amino-3-cyano-5-(phenylthio)indole, has been demonstrated as follows.

A. The compound was administered at a daily oral dose of 10 mg./kg. to mice for 7 days, starting 24 hours after subcutaneous innoculation of Walker tumour cells. At day 14 a 75% inhibition of tumour growth, compared to controls, was observed, there being no deleterious effect on body weight.

B. The compound was administered at a daily oral dose of 10 mg./kg. to mice for 5 days, starting 72 hours after subcutaneous innoculation of Walker tumour cells. At day 14 a 60% inhibition of tumour growth, compared to controls, was observed. There was little change in body weight.

C. At a single intraperitoneal dose of 132 mg./kg. the compound produced a 63% increase in survival time in mice innoculated with the L1210 leukaemia.

D. At intraperitoneal doses of 25 mg./kg. and 50 mg./kg. the compound produced 58% and 61% inhibitions respectively of tumour weight in mice innoculated with the ADJ/PC6 plasma cell tumour.

The good therapeutic ratio of the compound, relative to vincristine, can be measured in pregnant rats. The foeto-placental unit is, like cancer, a rapidly proliferating tissue which cytotoxic agents will destroy and thereby bring about pregnancy termination. The compound at a dose of 5 mg./kg. was fully effective in terminating pregnancy in rats when given twice on day 9 and once on day 10, either by the ora or subcutaneous route. No toxicity was observed until the dose was raised above 25 mg./kg. Vincristine was fully effective in this test at 0.25 mg./kg. and lethal at 0.5 mg./kg.

According to a further feature of the invention there is provided a pharmaceutical composition which comprises the indole derivative of the invention in association with a pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions (e.g. micronised suspensions), emulsions, dispersible powders, suppositories, sterile injectable aqueous or oily solutions or suspensions, gels, creams, ointments or lotions.

A preferred pharmaceutical composition of the invention is one suitable for oral administration in unit dosage form, for example a tablet or capsule which contains between 20 mg. and 500 mg. of the indole derivative, or one suitable for parenteral administration, for example a sterile injectable containing between 0.1% and 10% w/w of the indole derivative.

The pharmaceutical composition of the invention will normally be administered for the purpose of aiding regression or palliation of cancer in warm-blooded animals, including humans, in the same general manner as that employed for oncodazole, due allowance being made in terms of dose levels for the potency of the indole derivative of the present invention relative to oncodazole. There is no record of either vincristine or vinblastine being used to treat benign disease. However it is possible that a new agent of this type with a greater therapeutic ratio, i.e. the composition of the invention, may be useful to treat severely incapacitating benign, as well as malignant, proliferative disease, for example psoriasis. The composition for this indication may be oral or topical. Each human patient will receive an oral dose of between 40 mg. and 4 g., and preferably between 200 mg. and 2 g., of the indole derivative or a parenteral dose of between 10 mg. and 1 g., and preferably between 50 mg. and 500 mg. of the indole derivative, the composition being administered in the frequency range once per week to 1 to 3 times per day. Alternatively the composition may, for example, be given for several, for example three, successive days at intervals of, for example, seven days.

The invention is illustrated, but not limited, by the following Examples:

EXAMPLE 1

The sodium salt of 2-nitro-5-(phenylthio)-phenylmalonitrile (40 g., 0.126M.) was dissolved in dimethyl formamide (200 ml.) and added to a solution of NaHCO$_3$ (68.9 g., 0.82M.) in water (200 ml.). To this solution sodium dithionite (31.5 g., 0.164M.) was added in portions. Additional solid NaHCO$_3$ (68.9 g.) and sodium dithionite (31.5 g.) were added followed by sufficient aqueous dimethyl formamide (1:1 v/v) to ensure complete solution. T.l.c. showed the reaction was complete after stirring overnight. The reaction mixture was then poured into water (1500 ml.) and extracted with ethyl acetate (3×350 ml.). The combined extracts were washed with water (8×350 ml.), filtered through phase-separation paper and evaporated under reduced pressure to give an oil. The crude product was chromatographed on silica gel using toluene-ethyl acetate (1:1 v/v) as initial eluant, changing the ratio to (1:3 v/v) to give the product as an amorphous solid. Crystallisation from toluenemethanol gave colourless crystals of 2-amino-3-cyano-5-(phenylthio)indole, m.p. 191.5°–192° C. (12.65 g., 38%).

The sodium salt of 2-nitro-5-(phenylthio)-phenylmalononitrile used as starting material may be prepared as follows:

A solution of 2-nitro-5-(phenylthio)aniline (80 g., 0.325M.) in warm glacial acetic acid (600 ml.) and concentrated HCl (250 ml.) was added over an hour to a rapidly stirred mixture of crushed ice (1 l.) and concentrated HCl (250 ml.). The suspension was stirred overnight then cooled to 7° C. A chilled solution of NaNO$_2$ (22.4 g., 0.325M.) in water (50 ml.) was added over an hour. The reaction temperature was maintained below 12° C. and excess NaNO$_2$ (0.25 g.) was added to give a positive starch-iodide test. The solution of diazonium salt was added over 1.5 hours to a stirred solution of cuprous chloride (35.4 g., 0.357M.) in concentrated HCl (150 ml.) and water (110 ml.) at 25°–35° C. When the addition was complete the mixture was warmed to 50°

C. until N₂ evolution ceased, allowed to cool and extracted once only with toluene. This extract was washed with dilute aqueous HCl, water, dilute aqueous NaOH solution, then repeatedly with water (till the washings were neutral), then dried over anhydrous Na₂SO₄. Evaporation under reduced pressure gave a dark brown oil (78 g.) which was chromatographed on silica gel (2.5 kg.) using toluene-petroleum ether (b.p. 80°-100° C.) (1:2 v/v changing to 1:1 v/v) as eluant. The product, 2-chloro-4-(phenylthio)nitrobenzene, was obtained as a pale yellow oil (53.7 g., 62%) with a residual 0.1 mole toluene (NMR and microanalysis), and was used as such.

To a stirred solution of 2-chloro-4-(phenylthio)nitrobenzene (53.7 g., 0.2M.) and malononitrile (13.35 g., 0.2M.) in N-methylpyrrolidone (150 ml.) was added dropwise a solution of sodium hydroxide (16.18 g., 0.4M.) in water (16 ml.). The reaction mixture was stirred overnight; t.l.c. indicated the reaction was complete and it was then poured into rapidly stirred saturated brine solution (1 l.). The aqueous layer was extracted with ethyl acetate (2×500 ml.). The organic solutions were combined, evaporated under reduced pressure and the residue triturated with petroleum ether (b.p. 60°-80° C.) to give a very dark red crystalline solid. This was filtered off and washed with toluene (×3) and petroleum ether (b.p. 60°-80° C.) (×1) before being dried. The solid was purified by extraction with hot ethyl acetate (until the extracts were almost colourless) followed by evaporation and drying under high vacuum to give deep red crystals of the sodium salt of 2-nitro-5-(phenylthio)phenylmalonitrile (41.8 g., 65%).

EXAMPLE 2

To an ice-cooled solution of 2-amino-3-cyano-5-(phenylthio)indole (1.5 g., 5.7mM.) in dimethyl formamide (20 ml.) was added sodium hydride (0.27 g., 50% w/w dispersion in mineral oil, 5.7mM.) followed by ethyl phenyl carbonate (0.94 g., 5.7mM.). The mixture was stirred overnight and allowed to warm to room temperature. T.l.c. indicated the reaction was complete. The reaction mixture was poured into rapidly stirred water and neutralised with acetic acid. The cream-coloured precipitate was filtered off and dried to give the crude product (1.62 g.) m.p. 181°-2° C. Recrystallisation from ethanol gave colourless crystals of ethyl 3-cyano-5-(phenylthio)indol-2-ylcarbamate, m.p. 190.5°-191.5° C. (0.82 g., 43%).

FORMULAE

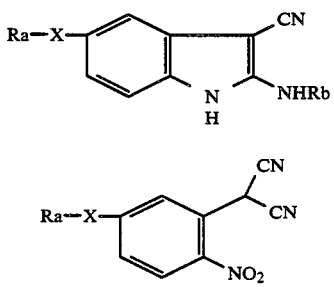

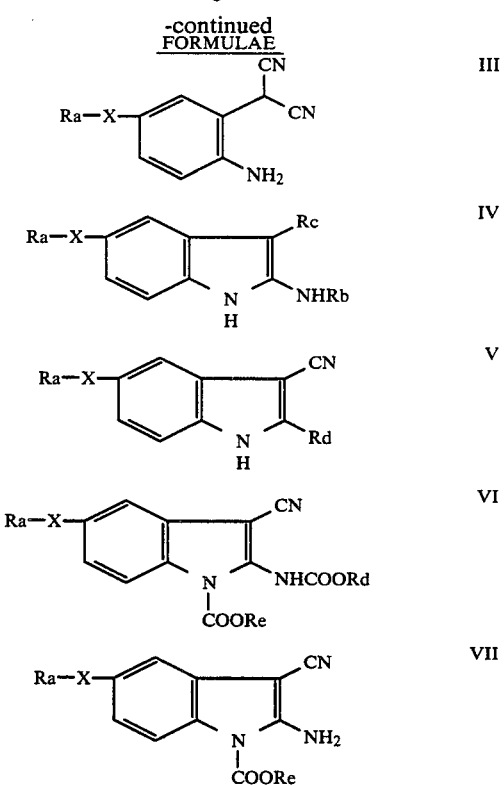

We claim:
1. An indole of the formula I:

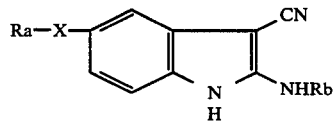

in which X is an oxygen or sulphur atom, Ra is a phenyl radical which is optionally substituted by one or two groups selected from halogen atoms and 1-6C alkyl, 1-6C alkoxy and trifluoromethyl radicals and Rb is a hydrogen atom or a 2-6C alkoxycarbonyl radical.

2. An indole of the formula I:

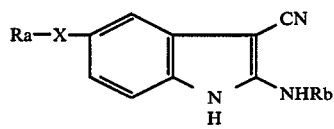

in which X is an oxygen or sulphur atom, Ra is a phenyl radical which is optionally substituted by one or two groups selected from fluorine, chlorine and bromine atoms and methyl, methoxy and trifluoromethyl radicals and Rb is a hydrogen atom or a methoxycarbonyl or ethoxycarbonyl radical.

3. An indole as claimed in claim 1 in which Ra is an unsubstituted phenyl radical and Rb is a hydrogen atom.

4. 2-Amino-3-cyano-5-(phenylthio)indole.

5. A pharmaceutical composition which comprises an indole as claimed in claim 1 in association with a pharmaceutically-acceptable diluent or carrier.

6. A method of aiding regression or palliation of Walker tumor, leukaemia, or plasma cell tumor in warm-blooded animals, including humans, which comprises administration of a therapeutically-effective amount of the compound of claim 1.

* * * * *